United States Patent [19]

Fleming

[11] Patent Number: 5,098,846
[45] Date of Patent: Mar. 24, 1992

[54] SOLID PHASE PROTEIN ASSAY BY SOLID PHASE FREE SITE TITRATION

[75] Inventor: Nigel Fleming, Arlington, Mass.
[73] Assignee: McLean Hospital, Boston, Mass.
[21] Appl. No.: 54,635
[22] Filed: May 27, 1987
[51] Int. Cl.$^5$ .................. G01N 31/16; G01N 33/548
[52] U.S. Cl. ...................................... 436/86; 436/163; 436/518; 436/530
[58] Field of Search ............... 436/518, 527, 529, 530, 436/807, 808, 809, 86, 163; 435/177; 530/810, 812

[56] References Cited

U.S. PATENT DOCUMENTS

| | | | |
|---|---|---|---|
| 3,720,760 | 3/1973 | Bennich et al. ............... | 436/513 X |
| 4,020,151 | 4/1977 | Bolz et al. ..................... | 436/527 |
| 4,254,096 | 3/1981 | Monthony et al. ............ | 424/8 |
| 4,279,885 | 7/1981 | Reese et al. .................. | 424/1.1 |
| 4,380,580 | 4/1983 | Boguslaski et al. ........... | 435/7 |
| 4,496,654 | 1/1985 | Katz et al. .................... | 435/7 |
| 4,624,916 | 11/1986 | Shah et al. .................... | 436/530 X |
| 4,672,024 | 6/1987 | Glaever et al. ................ | 436/810 X |
| 4,693,985 | 9/1987 | Degen et al. .................. | 436/531 |
| 4,990,442 | 2/1991 | Del Campo .................... | 435/7.5 |

OTHER PUBLICATIONS

Laboratory Techniques in Biochemistry and Molecular Biology, Bardon, R. H. and P. H. van Knippenberg, Elsevier (1984), pp. 42–47.
The International Search Report for the Corresponding PCT Application No. PCT/US88/01802.
Sandwick et al., Anal. Biochem. 147:210–216 (1985).
Nakamura et al., Anal. Biochem. 148:311–319 (1985).
Wolff et al., Anal. Biochem. 147:396–400 (1985).
Suresh et al., Anal. Biochem. 151:192–195 (1985).
Sportsman et al., Anal. Biochem. 139–300 (1984).
Hawkes et al., Anal. Biochem. 119:142–147 (1982).
Kuno et al., Nature (London) 215:974–975 (1975).
Bramhall et al., Anal. Biochem. 31:146–148 (1969).
Pristoupil, Nature (London) 212:75–76 (1966).
Kumar et al., Biochem. Biophys. Res. Commun. 131:883–891 (1985).
Hancock et al., Anal. Biochem., 133:157–162 (1983).
Yuen et al., Anal. Biochem. 126:398–402 (1982).
Kittler et al., Anal. Biochem. 137:210–216 (1984).
Bradford, M. M., Anal. Biochem. 72:248–254 (1976).
Scopes, R. K., Anal. Biochem. 136:525–529 (1984).
Ahmad et al., Anal. Biochem. 148:533–541 (1985).
Krystal et al., Anal. Biochem. 148:451–460 (1985).
Kaplan et al., Anal. Biochem. 150:97–104 (1985).
Schaffner et al., Anal. Biochem. 56:502–514 (1973).
Redinbaugh et al., Anal. Biochem. 147:144–147 (1985).
Gershoni et al, Anal. Biochem. 131:1–15 (1983).

Primary Examiner—David Saunders
Attorney, Agent, or Firm—Sterne, Kessler, Goldstein & Fox

[57] ABSTRACT

The invention relates to a quantitative assay for an analyte which comprises contacting a sample containing an analyte with a solid phase support to immobilize said analyte, following by indirectly quantitating the presence of bound analyte by titrating the unoccupied binding sites with a titrating protein which is detectably labeled.

5 Claims, 14 Drawing Sheets

DISK WITH FREE BINDING SITES

ADSORB SAMPLE PROTEIN

HIGH CONCENTRATION          LOW CONCENTRATION

TITRATE FREE SITES WITH RADIOLABELLED PROTEIN

LOW BINDING OF LABEL          HIGH BINDING OF LABEL

SOLID PHASE PROTEIN ASSAY BY SOLID PHASE FREE SITE TITRATION

FIELD OF THE INVENTION

The invention relates to a method for the assay of an analyte which may be present in a sample by binding the analyte to a solid phase support and titrating the limited free binding sites of the solid phase support with a labeled molecule.

BACKGROUND OF THE INVENTION

The use of dot assays and Western blots have become widespread in biochemical laboratories. In many cases, their use has been limited to screening methods for immunoreactive proteins. There is an increasing trend towards quantitation using these methods by autoradiography or dye-based densitometry. However, the problem of determining the total protein content on nitrocellulose matrices has only recently received any attention which is due, in part, to the development of new protein assay methods. Such determinations have considerable value for a variety of applications.

In recent years, a number of new methods for the assay of protein have been published that offer either increased sensitivity or facility over older methods like the Biuret method (Itzhaki, R.F., et al., *Anal. Biochem.* 9:401-410 (1964)) and Lowry's method (Lowry, O.H., et al., *J. Biol. Chem.* 193:265-275 (1951)). Notably, the method introduced by Bradford (*Anal. Biochem.* 72:248-254 (1976)) has been popular. This method exploits the protein-binding properties of dyes, which have long been utilized in gel electrophoresis, for the visualization of protein bands and, more recently, in differential adsorption of proteins by dye adsorption chromatography (see Scopes, R.K., *Anal. Biochem.* 136:525-529 (1984) for example). Variations of the Bradford assay are reported for the quantitation of proteins immobilized on immunoadsorbents by elution of protein-bound dye under harsh conditions. Ahmad, H., et al., *Anal. Biochem.* 48:533-541 (1985).

Krystal et al., *Anal. Biochem.* 48:451-460 (1985), report a sensitive protein stain for the assay of protein solutions. This assay permits nanogram quantities of proteins to be determined. High sensitivity is critical for the quantitation of proteins, produced from large-scale purifications, which may be present in the order of micrograms. However, the Krystal assay suffers from being prone to rather a large number of interfering substances common to biochemical samples, which require removal before the assay.

Interest in the use of protein binding dyes for the assay and affinity purification of proteins has spurred new methodologies. Kaplan and Pedersen, *Anal. Biochem.* 150:97-104 (1985) report a modification of an earlier procedure (Schaffner, W., et al., *Anal. Biochem.* 56:502-514 (973)) using amido black dye. Another dye-binding protein assay was developed by Redinbaugh and Campbell (*Anal. Biochem.* 147:144-147 (1985)) which utilized microtiter plates in a similar manner to ELISAs.

Since polyvinyl chloride (microtiter plates) became predominantly replaced by nitrocellulose (and other matrices like nylon and diazotized cellulose) for protein adsorption (Gershoni, J.M., et al., *Anal. Biochem.* 131:1-15 (1983)), the use of immunodot assays on nitrocellulose has become widespread (Hawkes, R., et al., *Anal. Biochem.* 119:142-147 (1982) and Suresh, M.R., et al., *Anal. Biochem.* 151:192-195 (1985)). Nakarmur et al. (*Anal. Biochem.* 311-319 (1985)) reported a similar method of spotting nitrocellulose with protein, and staining the total protein thus adsorbed with dye (amido black or Ponceau red), with subsequent densitometry. This method was extremely rapid, sensitive, and, unlike spectrophotometric proteins assays, was almost without interference from common laboratory chemicals. This method allows samples containing 0.05-10 ug to be detected (a 200 fold range). Another such assay was disclosed by Sportsman, J.R., et al., *Anal. Biochem.* 139:298-300 (1984), which involved detection by laser densitometry. However, different sample proteins give standard curves with different slopes. These assays are affected by both differential adhesion of proteins to nitrocellulose and differential dye-binding properties of each sample protein. Thus, differential protein adhesion remains a limitation of such nitrocellulose-based protein assays.

Protein assays using nitrocellulose filters have also been reported by Kuno, H., et al., *Nature (London)* 215:974-975 (1967); Bramhall, S. et al., *Anal. Biochem.* 31:146-148 (1969); and Pristoupil, T.I. et. al., *Nature (London)* 212:75-76 (1966). These assays involve elution of stained protein samples for spectrophotometry (Kuno, *supra*), or calculation of the area of each stained spot (Pristoupil, *suora*). Both of these quantitation methods limit the usefulness of the method.

Kumar, B.V., et al., *Biochem. Biophys. Res. Commun.* 131:883-891 (1985) disclose quantitation of proteins on nitrocellulose by iodination with chloramine-T and potassium iodide. The bound iodine is then detected with starch solution. Hancock, K., et al., *Anal. Biochem.* 33:157-162 (1983), disclose a method for the qualitative determination of proteins on Western blots by transfer onto nitrocellulose and staining with india ink. Yugn, K.C., et al., *Anal. Biochem.* 126:398-402 (1982), disclose a method for the detection of nanogram quantities of proteins by transfer of the protein from a Western blot to nitrocellulose, followed by staining with a silver solution. Kittler, J.M., et al., *Anal. Biochem.* 137:210-216 (1984), disclose an immunochemical method for detecting proteins on blots which involves derivatizing the protein with a group recognized by an antibody, followed by detection. However, all of these methods suffer from the disadvantage that the sample protein is chemically modified by the assay, thus making recovery of the sample protein either very difficult or impossible.

Another method for quantitation of proteins on nitrocellose is taught by Wolff, et al., *Anal. Biochem.* 147:396-400 (1985). In this method, TNP (2,4,6-trinitrobenzene sulfonic acid) is used to derivatize the proteins that are immobilized on the nitrocellulose support. Anti-TNP serum is then added as a first antibody and incubated so that the first antibody will attach to the TNP-modified proteins. Anti-IgG-peroxidase conjugate is added as a second antibody. Color is then developed to detect the protein. The proteins immobilized on nitrocellulose are directly measured by measuring the resultant color. However, this method suffers from the requirement for antibodies.

U.S. Pat. No. 4,279,885 to Reese et al., describes a solid phase competitive protein binding assay where an antigen or hapten can be assayed. The method involves competition between the analyte and a labeled form thereof for a limited number of receptor or binding sites which are immobilized to a solid support. The assay may be conducted by mixing the components simultaneously or sequentially. The sequential assay involves contacting a solution of an analyte with a support containing immobilized receptors or antibodies, followed by contacting the mixture with a tracer. The tracer may be the analyte, or analog thereof, which contains a label or tag.

Quantitative assays which do not utilize antibodies are preferable. For example, a sample containing protein to be assayed is mixed with a marker protein on contact with a polystyrene latex. A competition is created between the marker enzyme and the analyte protein for the limited surface binding sites. The amount of enzyme remaining in the supernatant is then determined. The inactivation of the enzyme upon binding to the hydrophobic latex surface allows measurement of the bound/free enzyme ratio, and thus, the competing protein concentration. Sandwick, et al., Anal. Biochem. 147:210-216 (1985). However, different proteins have markedly different affinities for solid supports. Thus, it is necessary to construct a standard curve for each protein which is to be quantified. In addition, relatively significant amounts of proteins are required for this assay. Thus, this method is not practical for quantitation of trace quantities of isolated proteins which may comprise only a few micrograms obtained from hundreds of litres of fermentation broth.

Thus, it would be desirable to have a quantitative assay which is fast and reliable, requires only minimal amounts of analyte, and does not chemically modify the analyte.

SUMMARY OF THE INVENTION

The invention relates to a method for detecting and quantitating an analyte, which includes
 (a) immobilizing an analyte to be detected and quantitated onto a solid phase support;
 (b) contacting said solid phase support-immobilized analyte with a detectably labeled titrating protein to bind to the unoccupied free binding sites;
 (c) incubating said detectably labeled titrating protein with said support for a sufficient amount of time to allow said titrating protein to bind to a portion of the unoccupied binding sites of the solid phase support;
 (d) separating said solid support from the incubation mixture obtained in step (c); and
 (e) detecting the bound titrating protein and thereby detecting and quantifying the analyte.

The invention also relates to a kit for the quantitation of an analyte in a sample comprising a carrier being compartmentalized to receive in close confinement therein
 a) a solid support capable of binding an analyte;
 b) a second container contains washing buffers; and
 c) a third container contains a detectably labeled titrating protein which irreversibly binds to the unoccupied sites on said solid support.

The invention offers a convenient, flexible and rapid method to detect and quantify analytes in solution. In addition, the method of the present invention allows quantitation of proteins immobilized on a solid phase support such as a Western blot. Other advantages include accommodation of a large range of protein concentrations, the minimum sample requirement, the rapidity of processing large numbers of samples, and the ability to detect practically unlimited signal. This solid phase protein assay also offers the advantage of reducing the blank value by batch washing. Moreover, since the present invention does not utilize detection methods such as antibody-binding, dye-binding, silver binding, or iodination which tend to destroy the sample, the unaltered analyte may be recovered.

In addition, since most traditional solid phase assays are very sensitive to interfering substances, the analyte must be separated from such substances prior to the assay. Such separations are time consuming, often ineffective, and may result in damage to an analyte such as interferon. Thus, the present invention offers a considerable advantage over traditional assays since the assay is not affected by such substances. Moreover, many assays are affected by the nature of the buffer solution containing the analyte. If the buffer is not known, it may not be appropriate to compare the results of the assay to a standard curve. The present invention overcomes this limitation since it is unaffected by the nature of the buffer which contains the analyte.

DESCRIPTION OF THE PREFERRED EMBODIMENTS

This invention is directed towards methods of quantitating an analyte by immobilizing said analyte on a solid phase support, followed by contacting the solid phase support with a detectably labeled titrating molecule which is capable of being immobilized to said support, and detecting the amount of detectably labeled titrating molecule immobilized to the unoccupied sites on the solid support.

By "solid phase support" is intended any solid support capable of immobilizing an analyte. Such supports include but are not limited to nitrocellulose, diazocellulose, glass, polystyrene, polyvinylchloride, polypropylene, polyethylene, dextran, Sepharose, agar, starch, nylon and microtitre plates. Preferred solid phase supports include nitrocellulose and diazocellulose. However, the invention is not limited only to the use of these supports, it being within the ability of one having ordinary skill in the art to determine other solid phase supports which are capable of immobilizing analytes or will be able to ascertain the same by the use of routine experimentation. Such solid phase supports can advantageously be fixed to a dip stick.

By "analyte" is intended any molecule that can be immobilized on a solid phase support which results in the blocking of binding sites on said support. In a preferred embodiment, said analyte is a protein. However, the invention is not limited to assay for only a protein analyte. Those skilled in the art will note that many other suitable analytes which bind to solid supports and block the free sites may be quantitated by this invention, or will be able to ascertain the same by use of routine experimentation.

By "titrating molecule" is intended any molecule which is capable of being detectably labeled or stained with a dye and which bind to a solid phase support. Foremost among such titrating molecules are titrating proteins. However, the invention is not limited to the use of proteins as titrating molecules, it being within the ability of one of ordinary skill in the art to determine other molecules which bind to a solid phase support. Suitable titrating proteins include, but are not limited to, antibodies, preferably IgG, antiantibodies, azocasein, or proteins commonly used as molecular weight markers. Preferable titrating proteins are IgG and azocasein which are strongly adhesive to the binding sites on nitrocellulose.

By "wash buffer" is intended any commonly used pH stabilized biological buffer which includes, but is not limited to Tris, Bis, phosphate buffers and the like. One of ordinary skill in the art will be able to ascertain other wash buffers useful in the practice of the invention, without undue experimentation.

Figure 10:
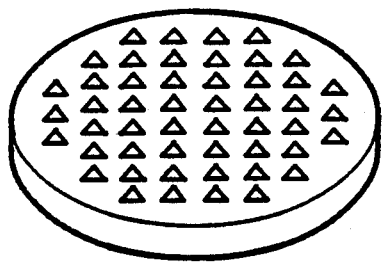
FIG. 10. This figure shows a representation of the protein assay.
Figure 10:
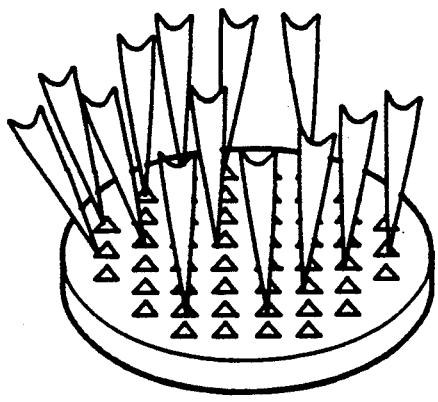
Figure 10:
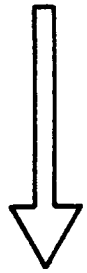
Figure 10:
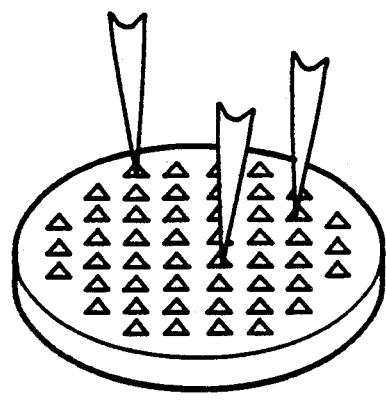
Figure 10:
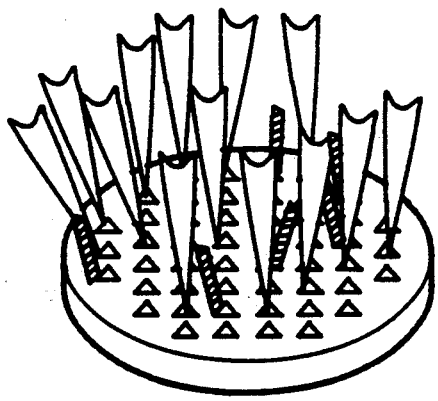
Figure 10:
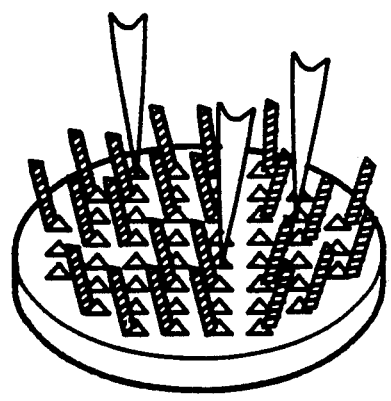

A figurative representation of the assay appears in FIG. 10. Disks of a solid support such as nitrocellulose have a fixed number of protein binding sites. When a sample, such as one containing a protein, is absorbed onto the disk, the number of free sites are reduced due to the protein binding to these sites. This binding is proportional to the amount of sample added. At high sample protein concentrations, very few binding sites remain. At low protein concentrations, many free sites remain. The free sites are titrated with, for example, a radiolabeled protein. Thus, the high sample protein disks incorporate fewer counts than the lower protein disks.

In one embodiment, the analyte is a protein. The sample containing the protein is contacted with nitrocellulose to effect immobilization of the sample protein by dot-blotting the sample onto the support, incubation of the support with a protein solution, or by electrotransfer of the protein from a gel onto the support. The nitrocellulose is then washed with suitable buffers, followed by contacting with a detectably labeled titrating molecule to titrate the unoccupied binding sites left on the nitrocellulose. The support is then washed again with a buffer, and the labeled titrating molecule detected.

The amount of bound analyte is determined indirectly by measuring the amount of label associated with the titrating molecule which binds to the unoccupied binding sites. The amount of analyte present in a sample is inversely proportional to the amount of label present. Standard solutions of analytes may be used to prepare a standard curve with the concentration of the analyte plotted on the abscissa and the detection signal on the ordinate. The results obtained from a sample containing analyte may be interpolated from such a plot to give the concentration of the analyte.

There are many different labels and methods of labeling known to those of ordinary skill in the art. Examples of the types of labels which can be used in the present invention include, but are not limited to, enzymes, radioisotopes, dyes, fluorescent compounds, chemiluminescent compounds, bioluminescent compounds and metal chelates. Those of ordinary skill in the art will know of other suitable labels for binding to the titrating molecule, or will be able to ascertain the same by the use of routine experimentation. Furthermore, the binding of these labels to the titrating molecule can be accomplished using standard techniques commonly known to those of ordinary skill in the art.

One of the ways in which the titrating molecule of the present invention can be detectably labeled is by linking the same to an enzyme. This enzyme, in turn, when later exposed to its substrate, will react with the substrate in such a manner as to produce a chemical moiety which can be detected as, for example, by spectrophotometric, fluorometric or by visual means. Enzymes which can be used to detectably label the titrating molecule of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The titrating molecule of the present invention is preferably labeled with a radioactive isotope which can be determined by such means as the use of a gamma counter or a scintillation counter or by autoradiography. Isotopes which are particularly useful for the purpose of the present invention are: $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to label the titrating molecule with a fluorescent compound. When the fluorescently labeled titrating protein is exposed to light of the proper wave length, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The titrating molecule of the invention can also be detectably labeled using fluorescent emitting metals such as $^{152}$Eu, or others of the lanthanide series. These metals can be attached to the protein molecule using such metal chelating groups as diethylenetriaminepentaacetic acid (DTPA) or ethylenediaminetetraacetic acid (EDTA).

The titrating molecule of the present invention also can be detectably labeled by coupling it to a chemiluminescent compound. The presence of the chemiluminescent-tagged titrating protein is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the titrating molecule of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Another technique which may also result in greater sensitivity when used in conjunction with the present invention consists of coupling the titrating molecule of the present invention to low molecular weight haptens. The haptens can then be specifically detected by means of a second reaction. For example, it is common to use such haptens as biotin (reacting with avidin) or dinitrophenyl, pyridoxal and fluorescamine (reacting with specific antihapten antibodies) in this manner. Amplification strategies may be readily applied to these and other labels.

For the purposes of the present invention, the analyte which is quantitated by this assay may be present in a sample solution or a gel matrix.

The assay of the present invention is ideally suited for the preparation of a kit. Such a kit may comprise a carrier means being compartmentalized to receive in close confinement therewith one or more container means such as vials, tubes and the like, each of said container means comprising the separate elements of the immunoassay. For example, there may be a container means containing a solid phase support, and further container means containing the detectably labeled titrating molecule in solution. Further container means may contain standard solutions comprising serial dilutions of analytes to be detected. The standard solutions of these analytes may be used to prepare a standard curve with the concentration of the analyte plotted on the abscissa and the detection signal on the ordinate. The results obtained from a sample containing an analyte may be interpolated from such a plot to give the concentration of the analyte.

In carrying out the titrating assay of the present invention on a sample containing an analyte, the process comprises:

a) contacting a sample suspected containing an analyte with a solid support to effect immobilization of the analyte:

b) contacting said solid support with a detectably labeled titrating molecule to bind with the remaining unoccupied binding sites;

c) incubating said detectably labeled titrating molecule with said support for a sufficient amount of time to allow said titrating molecule to bind to the unoccupied sites of the solid phase support;

d) separating the solid phase support from the incubation mixture obtained in step c); and e) detecting the bound titrating molecule and thereby detecting and quantifying the analyte.

Of course, the specific concentrations of detectably labeled titrating molecule and analyte, the temperature and time of incubation, as well as other assay conditions may be varied, depending on various factors including the concentration of analyte in the sample, the nature of the sample, and the like. Those skilled in the art will be able to determine operative and optimal assay conditions for each determination by employing routine experimentation.

Detection of the titrating molecule may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

For very dilute samples, multiple additions of sample may be applied to the solid phase support. When using nitrocellulose for dot-blot applications, 5-20 ul of sample may be used. However, when using larger volumes of sample, as when the support is incubated in the sample solution, the area of nitrocellulose may be increased accordingly. Thus, a considerable range of protein concentrations may be detected.

Other such steps as washing, stirring, shaking, filtering and the like may be added to the assays as is customary or necessary for the particular situation. However, the washing time should be advantageously be kept to a minimum to ensure the smallest degree of sample elution.

In the practice of this invention, the titrating molecule used to bind to the unoccupied nitrocellulose sites after the analyte has been immobilized, should have a similar or lower binding affinity for nitrocellulose than the analyte. Suitable titrating molecules may be selected by one of ordinary skill in the art, without undue experimentation. These titrating molecules may be selected by spotting radiolabelled sample and following the counts through selected titration steps. If radiolabelled sample is not available, labeled primary antibodies specific for the titrating molecule may be used. Alternatively, if the primary antibody is not labeled, a second labeled antibody, which is specific to the first antibody, may be added. Elution of the analyte in the presence of titrating molecule is then monitored. The invention may advantageously be applied to western blot or dot assays. With western blot assays, the sample proteins are electroblotted onto the matrix rather than being spotted on or incubated with the sample. Since amido-black staining of the nitrocellulose absorbed sample does not affect the subsequent titration of unoccupied binding sites, western blot or dot assays may be first visualized with amido-black, then assayed according to the present invention.

The analyte and the detectably labeled titrating molecule may be recovered by a variety of means. Thus, recovery of a protein analyte, where such protein is obtained, for example, by extensive purification of a dilute solution, is possible. For example, the solid phase support may be treated with a chaotropic salt such as $MgCl_2$ to elute the titrating molecule and the analyte where both are proteins. The analyte may then be separated from the titrating molecule using standard separation techniques known to those of ordinary skill in the art. However, the invention is not limited to the use of $MgCl_2$, it being possible for one of ordinary skill in the art to determine other chaotropic salts or reagents which may be used to recover the analyte and titrating molecule without undue experimentation.

The various aspects of the invention are further described in the following examples. These examples are not intended to limit the invention in any manner.

EXAMPLES

MATERIALS AND METHODS

Crystalline bovine serum albumin (BSA, fraction V), lyophilized rabbit IgG, and 5% casein in solution were purchased from Sigma (St. Louis, MO). Lysozyme was purchased from Worthington (Freehold, NJ). High molecular weight protein standards for SDS gel electrophoresis were purchased from Bio-Rad (Richmond, CA). These protein standards include myosin, $\beta$-galactosidase, phosphorylase B, BSA, and ovalbumin. Nonfat dry milk was purchased from Carnation (Los Angeles, CA). Bovine serum was purchased from the local slaughterhouse and heat inactivated at 56° C. for 30 minutes (to inactivate complement) before storing at −20° C. Sheep antirabbit anti-serum was induced in sheep by standard procedures, and treated similarly to bovine serum. Spectrapor dialysis membrane tubing, Spectrapor (Los Angeles, CA), 3500 MW cut off, was used for dialysis. Falcon 3912 Microtest III flexible assay plates were purchased from Becton Dickinson (Oxnard, CA). Carrier-free sodium iodide-I125 (high pH, 50 mC/ml) was obtained from Dupont New England Nuclear (Boston, MA). Iodo-beads were purchased from Pierce Chemical Company (Rockford, IL). Nitrocellulose paper (filter type HA 0.45 um pore size) was purchased from Millipore Corporation (Bedford, MA). A 40% efficient Packard auto-gamma scintillation spectrometer 5220 was used to count radioactivity. Samples were added to polystyrene $12 \times 75$ mm culture tubes (Fisher, Pittsburgh, PA) for gamma counting. Screw cap polystyrene tubes of either 16 or 50 ml capacity were used for some incubations (Corning, New York, NY), while plastic trays were used for others as specified in the following examples. All other chemicals were of reagent grade and were purchased from either Sigma or Fisher.

All titrating and wash buffers utilized a base buffer of 50 mM Tris, 5 mM EDTA, and 0.01% sodium azide at pH 7.4. Four combinations were used which include: plain base buffer, 10% (v/v) bovine serum, 3% (w/v) BSA, and 5% (w/v) nonfat milk. The titrating buffers were supplemented with iodinated proteins as indicated in the following examples, while the homologous wash buffers had the tracer omitted.

Iodinations of titrating proteins were performed according to the general method of Markwell, M.A.K., Anal. Biochem. 125:427–432 (1982) as outlined by the suppliers of iodo-beads (polystyrene-immobilized chloramine T). Approximately 100 ug of protein was dissolved in 500 ul of 50 mM Tris-base, 5 mM EDTA, 0.01% sodium azide buffer, pH 7.4. Six buffer-washed iodo-beads and 250 uCi of sodium $I^{125}$ were added to the sample. The mixture was incubated at room temperature for 15 minutes with periodic mixing. The solution was aspirated from the tube, leaving the catalytic beads. The solution was then dialyzed extensively against the same diluent buffer until the TCA precipitate counts approached 90%. TCA precipitate counts were assessed by the addition of 1 mg of BSA carrier protein in 100 ul of Tris buffer, followed by 1 ml of ice-cold 10% TCA. The mixture was then centrifuged at $3000 \times g$ at 4° C. for 15 minutes. The pellet was then counted for radioactivity.

The dye-staining protein assay was performed according to Nakamura et al., Anal. Biochem. 148:311–319 (1985), which comprises staining the nitrocellulose-adhesive proteins with an organic solution of amido black, and destaining the background with the solvent containing no dye.

EXAMPLE 1

Optimized Assay Protocol for Dot Blotting onto Matrix

Figure 11:
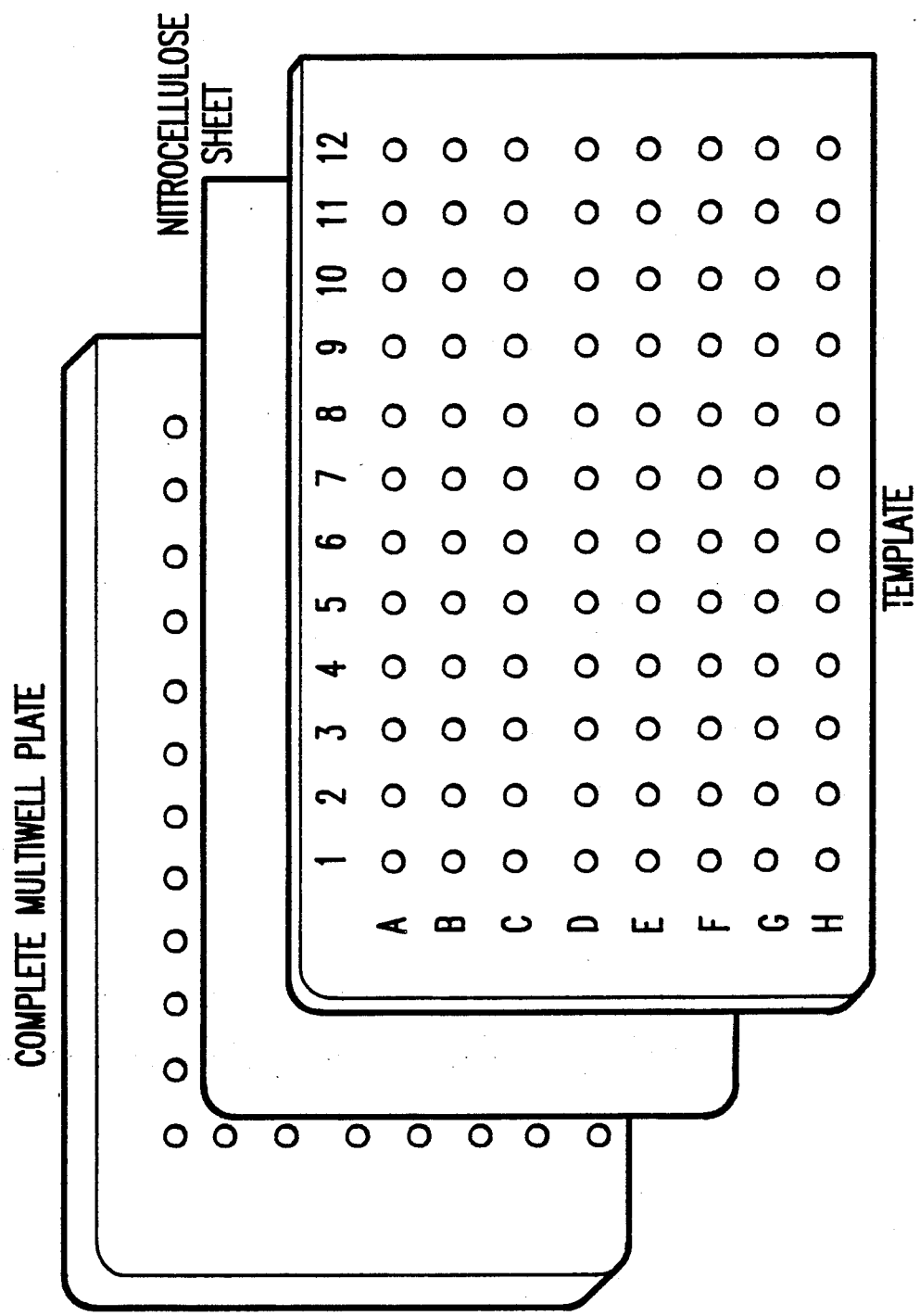
FIG. 11. This figure shows the device for holding a nitrocellulose sheet comprising a template and a 96-well tissue culture plate.

This example describes a protocol which is suitable for small sample volumes. A sheet of nitrocellulose (handled with gloves or forceps to prevent transfer of proteins from the skin), was placed onto a 96 well tissue culture plate with a numbered plastic template positioned over it using plastic bands (see FIG. 11). The template is fashioned by removing the wells and side walls from an intact plate. The plastic template prevents static cling and allows exact positioning of the samples. The template holes exactly match the size of the wells and the size of the final 5 ul volume sample when applied to the sheet. Since the holes of the template align exactly with the wells beneath and are the exact size of a 5μL spot, the sample does not touch any surface except the nitrocellulose. Samples were located on the nitrocellulose sheet by inclusion of 1% (v/v) stock phenol red and 1% (v/v) stock amido black dye into the sample. Stock dye solutions comprised 0.5 g of phenol red in 2 ml of Tris buffer and 0.1% amido black in methanol: acetic acid (4% v/v). Use of these dyes allows the sample circle to be visualized by the water-soluble phenol red which was subsequently removed during the washing step. The exact center of the circle was indicated by the small dot of amido black that survives the washing steps.

Five microliter spots of sample were applied to the nitrocellulose located over each tissue culture well. Each spot was thoroughly dried under a gentle air stream until no longer translucent (the test for dryness) for approximately 5 minutes. The nitrocellulose sheet containing 96 sample spots was then incubated in a shallow plastic box containing the titrating buffer (protein-free Tris) and iodinated protein (IgG-$I^{125}$, azocasein-$I^{125}$, mixed iodinated proteins) for 10–20 minutes to titrate the unoccupied sites. The nitrocellulose was then subjected to 3-2 minute washes in a protein wash buffer (5% nonfat milk, 3% BSA or 10% serum).

Samples were then harvested using a 7 mm cork borer which was centered on the small dye spot. The small sample disks were then counted for radioactivity. The samples were positioned at the bottom of the counting tube to ensure equal counting efficiency.

EXAMPLE 2

Sample Incubation With Nitrocellulose Disks

This example describes a protocol which is useful for larger volume samples. Nitrocellulose disks (7 mm), prepared using a standard office hole puncher, were transferred by a needle to a 15×75 mm polystyrene test tube. Sample protein (50–1000 ul) was added to the tube, then the tube vortexed briefly to ensure that the disk was fully immersed. The sample was incubated for 10 minutes, then washed by adding 1 ml of washing buffer (without tracer). The buffer was then aspirated, the tube vortexed, then the buffer aspirated a second time. This washing protocol was then repeated three times. Titrating buffer containing radioactive protein (100 ul) was incubated with the sample for 10–20 minutes. The sample was then washed three times with a wash buffer by aspiration and vortexing. The radioactivity bound to the disks wa then determined.

EXAMPLE 3

Optimization Trials--Fundamental Sample Dimensions After Spotting

Tris buffer was spiked with phenol red dye to visualize the sample spot on nitrocellulose. The weight of a photocopy of each spot was used to determine the area. The relation between the area and the volume of the sample was linear, while the relation between diameter of the spot and the sample volume was not. The area of the lower surface was greater than the upper surface (presumably due to gravity) which became more evident at sample volumes greater than 40 ul. These relations are described by the formula:

upper surface area $y = 0.55 X$; lower surface area $y = 0.81 X$ [where $y = $ area, $ = $ volume (ul) of sample]

Figure 1:
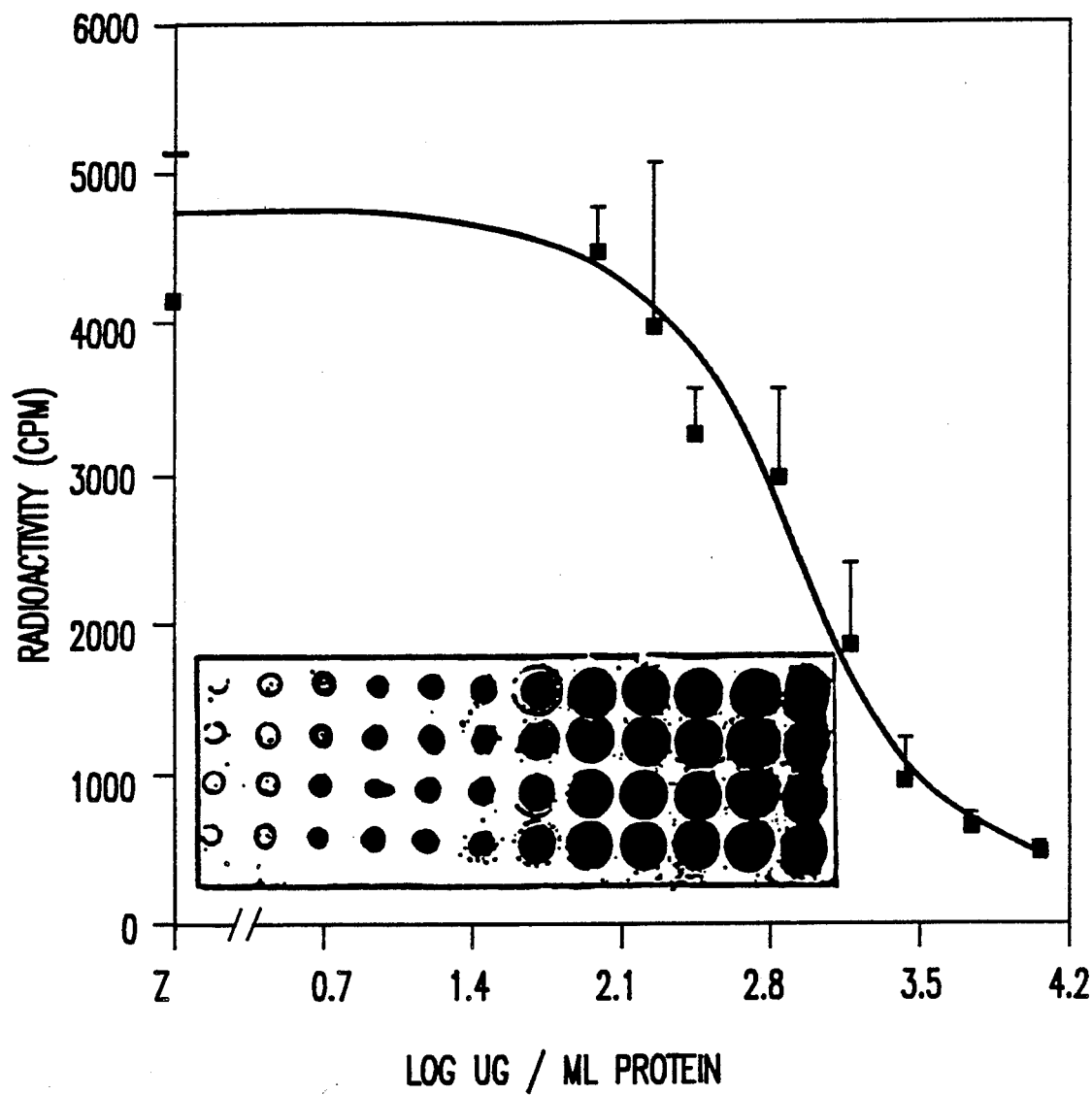
FIG. 1. This figure depicts a graph of the concentration of sample protein versus the radioactivity of immobilized titrating protein. Also depicted in the inset to FIG. 1 is the size of amido-black stained protein samples for a range of protein concentrations (from an undiluted sample to a 12th serial dilution).
Figure 2:
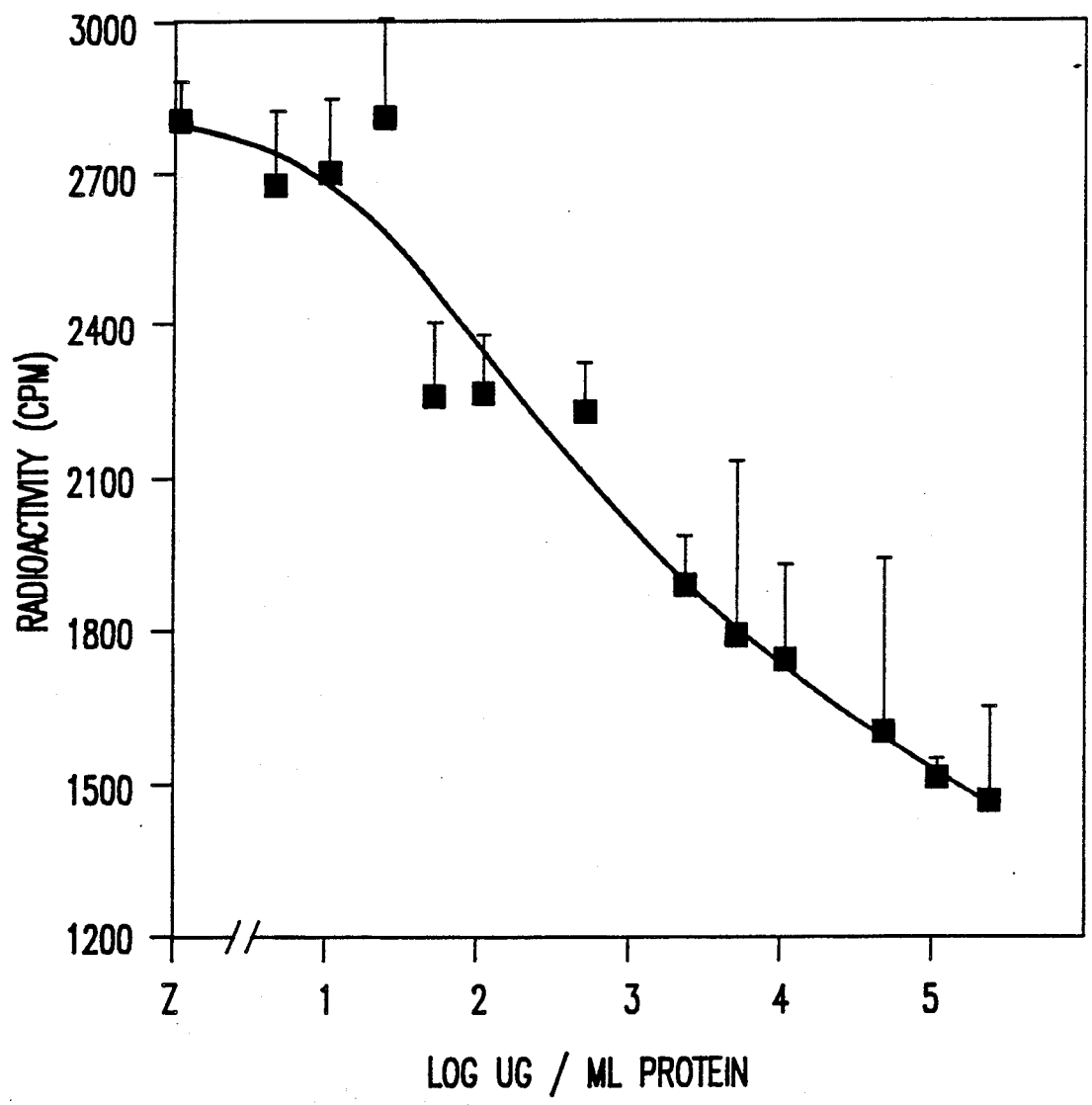
FIG. 2. This figure shows a standard curve for 5 ul aliquots of sheep anti-rabbit serum standard which range from undiluted to 1:16,384 dilution (70 mg/ml to 4 ug/ml protein). Unblocked free sites were titrated with iodinated azocasein.

The area of the spot did not change upon multiple additions if the sample spot was allowed to perfectly dry before the next sample was applied. The inset of FIG. 1 shows that the intensity of the amido-black stained protein on nitrocellulose, as well as the area of the spot, diminished with diminishing protein concentrations. This inset shows the size of quadruplicate amido-black staining protein samples which ranged from undiluted BSA to a 12th serial dilution. Z indicates a blank (no sample).

Also shown in FIG. 1 is a standard curve which depicts a graph of the concentration of sample protein versus the radioactivity of immobilized titrating protein. Disks of nitrocellulose were incubated for 40 min. (totally immersed) with 100 ul of BSA at concentrations which ranged from 10–156 ug/ml. One hundred ul of 10% bovine serum titration buffer containing iodinated azocasein was then added, and the mixture incubated for an additional 40 min. The disks were then rinsed vigorously in three vessels containing 10% bovine serum was buffer. The radioactivity on the disks was then counted.

Figure 3:
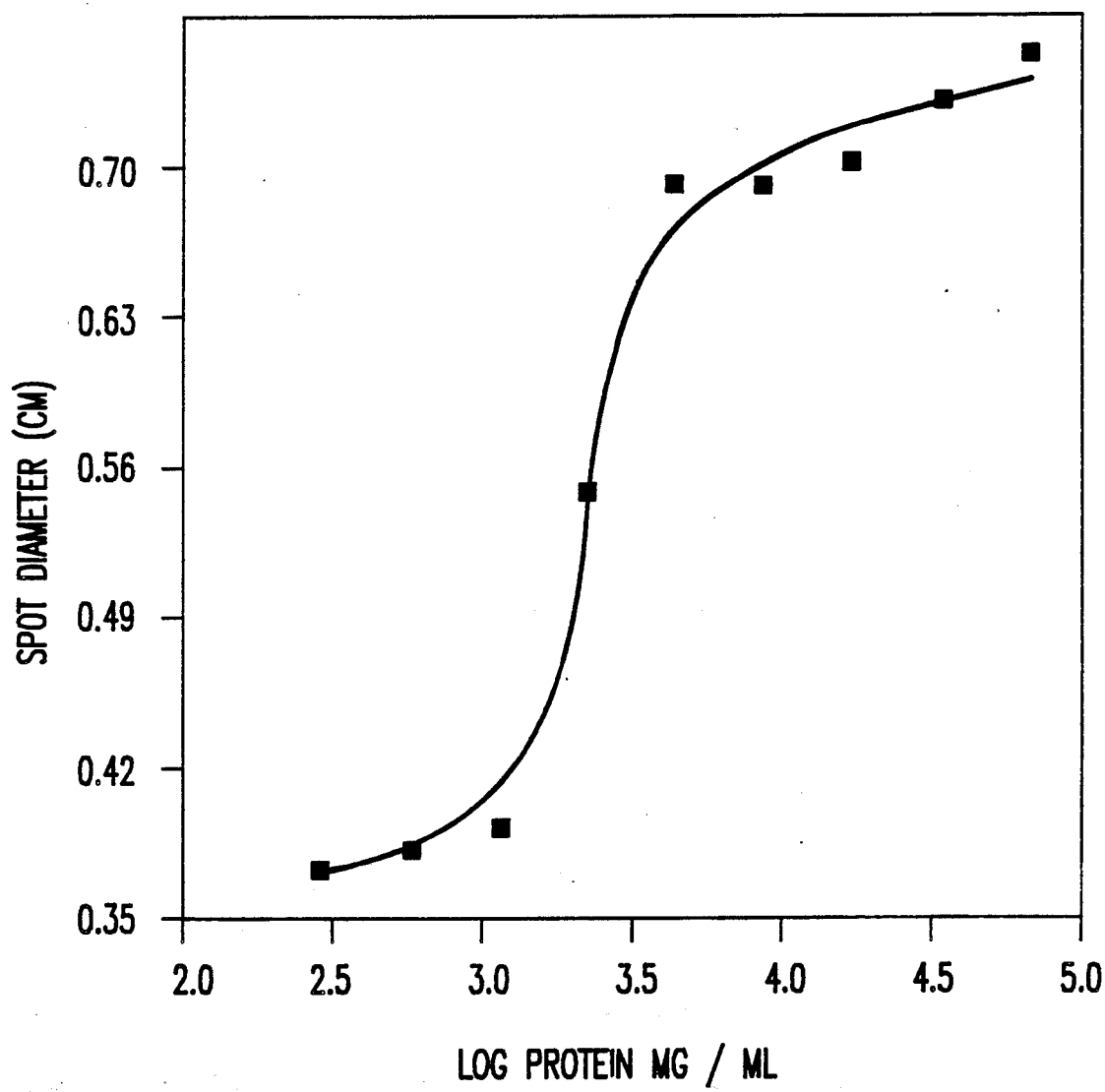
FIG. 3. This figure depicts a graph the diameter of amido-black stained protein sample spots on nitrocellulose versus the concentration of protein for serially diluted bovine serum protein samples.

FIG. 3 shows the diameter of amido-black stained protein sample spots on nitrocellulose following spotting of 5 ul of serially diluted bovine serum protein. Iodinated protein samples were spotted onto the nitrocellulose, dried, and incubated with 0.1% amido-black for several minutes after washing in acetic acid:methanol according to the method of Nakumura et al., suora. Between high (undiluted to 1:8 serum) and low (1:64–1:1256) protein concentrations, the diameter of the stained sample spots diminished gradually. However, the spot diameter reduced markedly at dilutions between 1:64–1:16. This result is probably due to a larger number of nitrocellulose binding sites remaining after immobilization of the sample protein which permits the titration assay to detect small changes in concentration. Even the gradual changes which occur at high or low protein concentrations are quantifiable.

Figure 4:
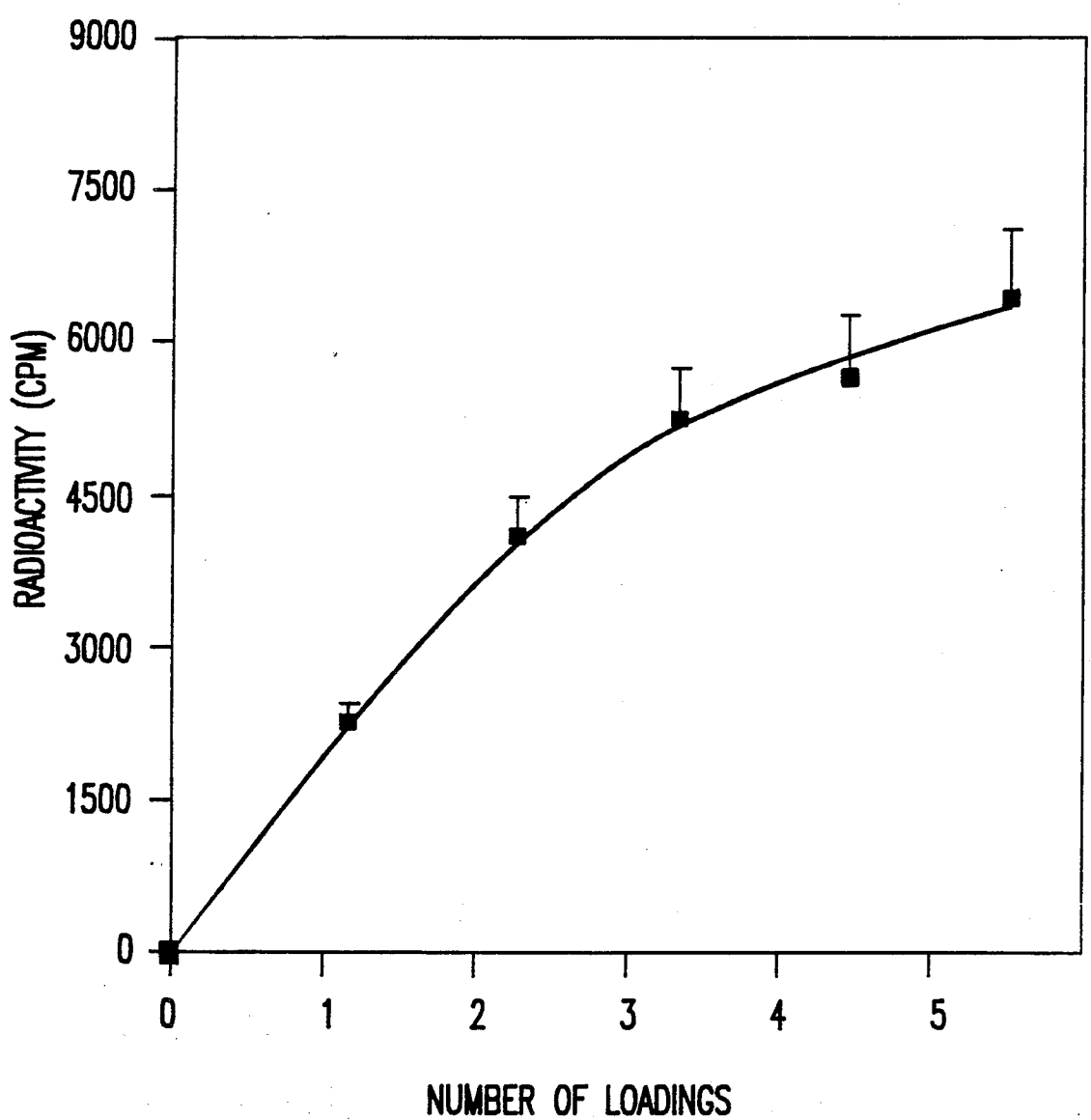
FIG. 4. This figure shows the effect of multiple additions of 5 ul aliquots of iodinated azocasein tracer in 10% bovine serum buffer, added to nitrocellulose, on the amount of bound radioactivity.
Figure 5A:
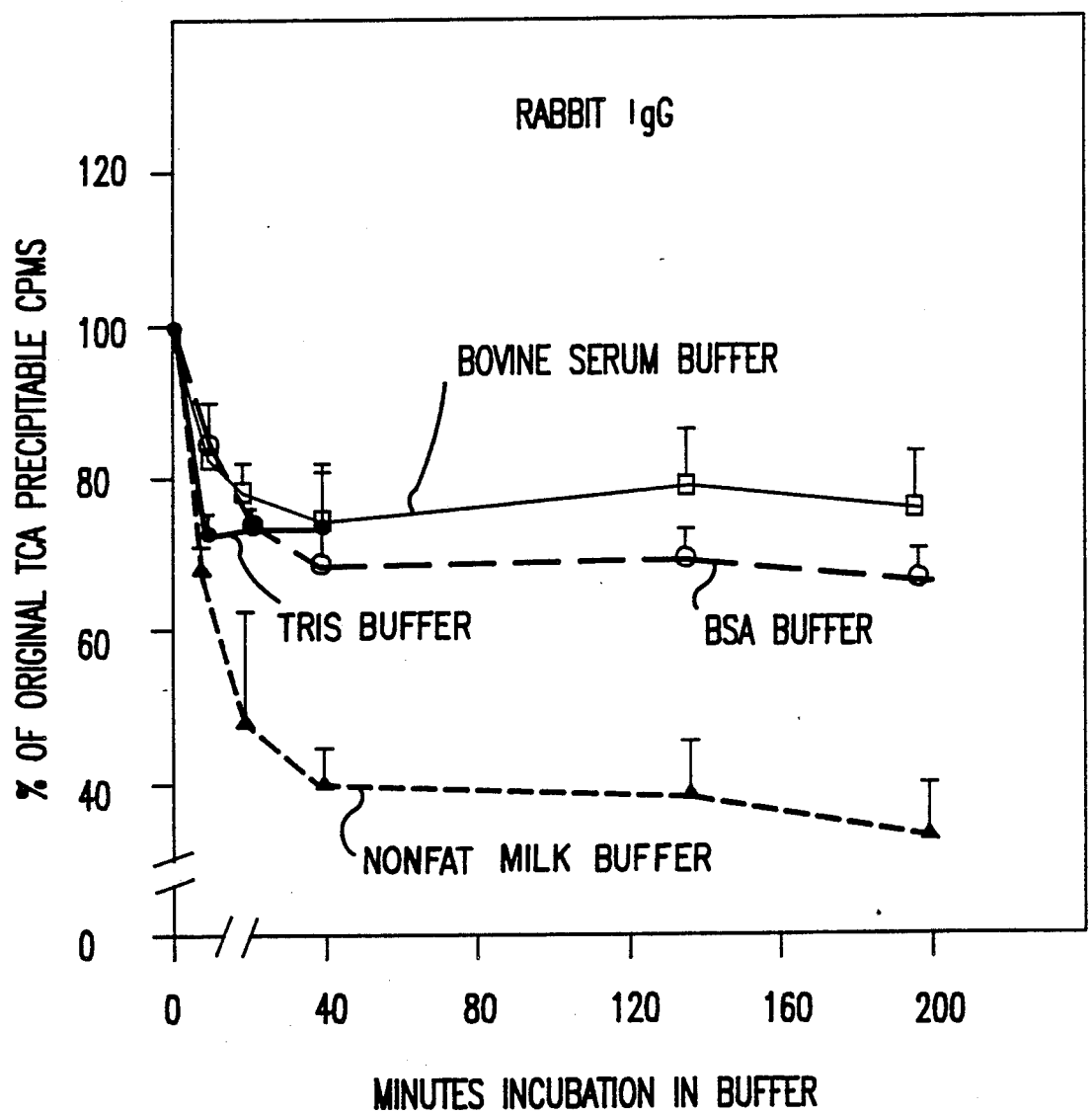
FIG. 5. This figure shows the amount of iodinated protein immobilized onto nitrocellulose expressed as a percentage of original TCA precipitable proteins, over time, in bovine serum buffer, bovine serum albumin buffer, nonfat milk buffer, and Tris buffer. Iodinated rabbit IgG, azocasein, molecular weight markers, and sheep anti-rabbit serum were tested.
Figure 5B:
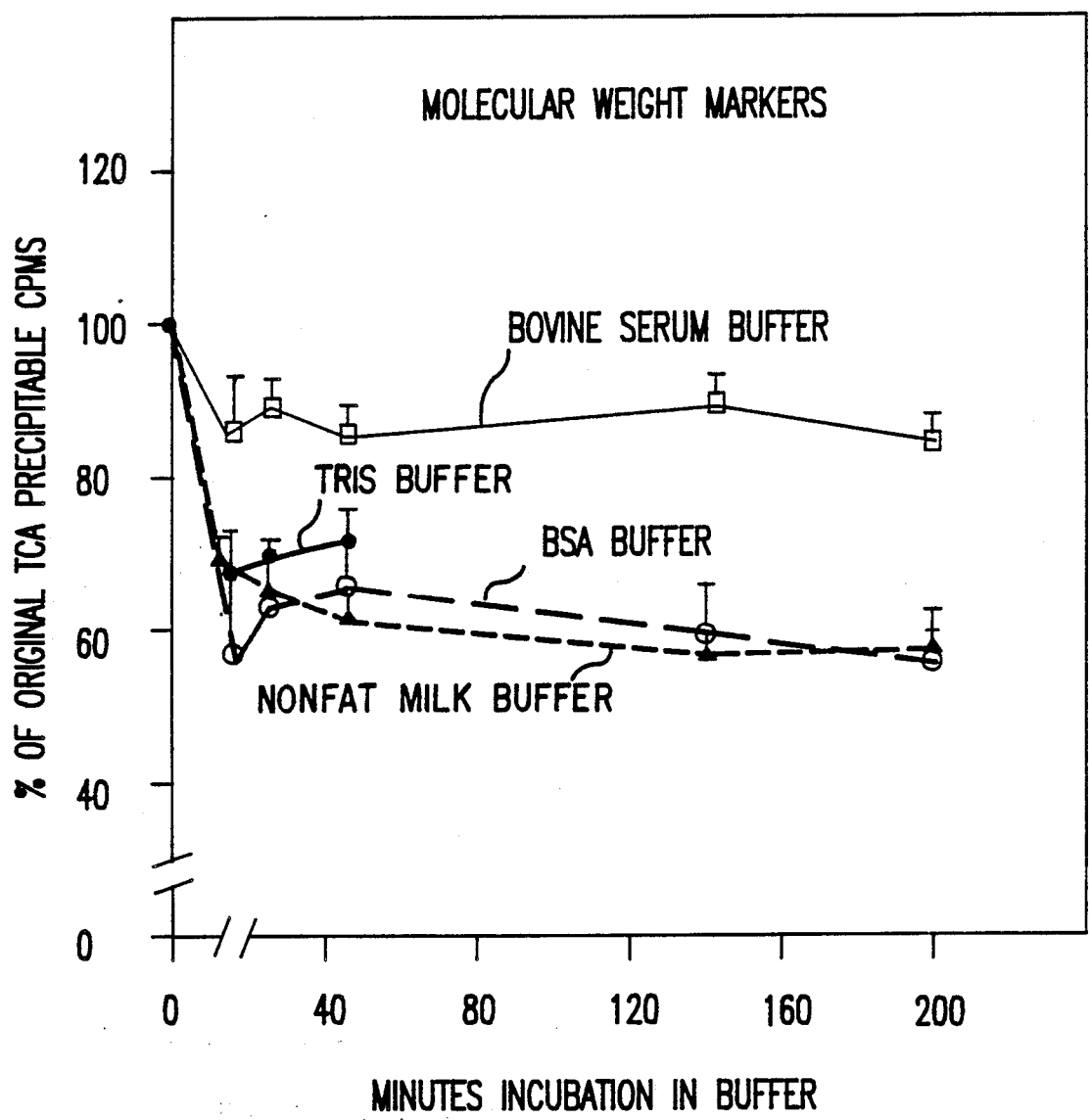
Figure 5C:
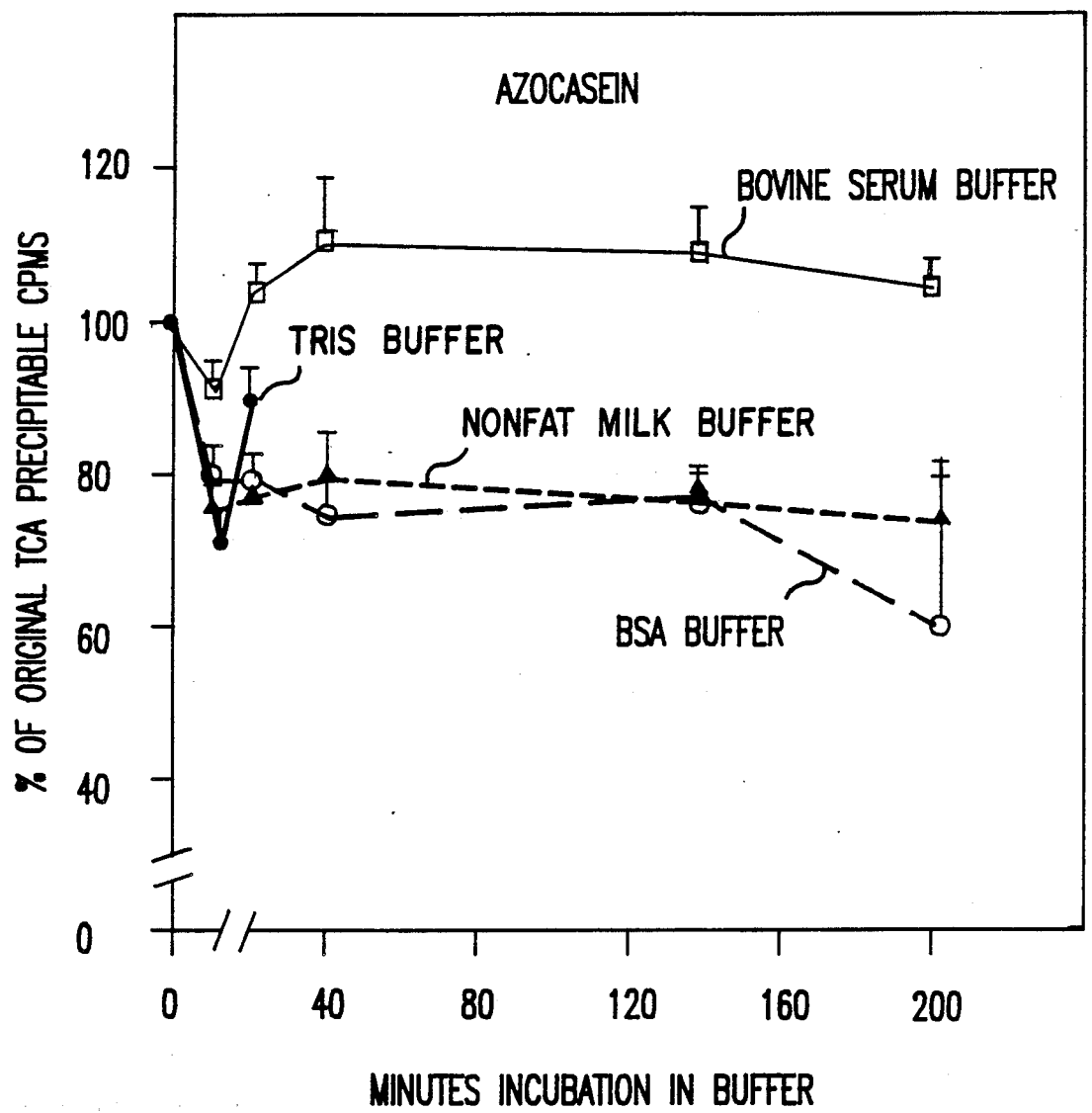
Figure 5D:
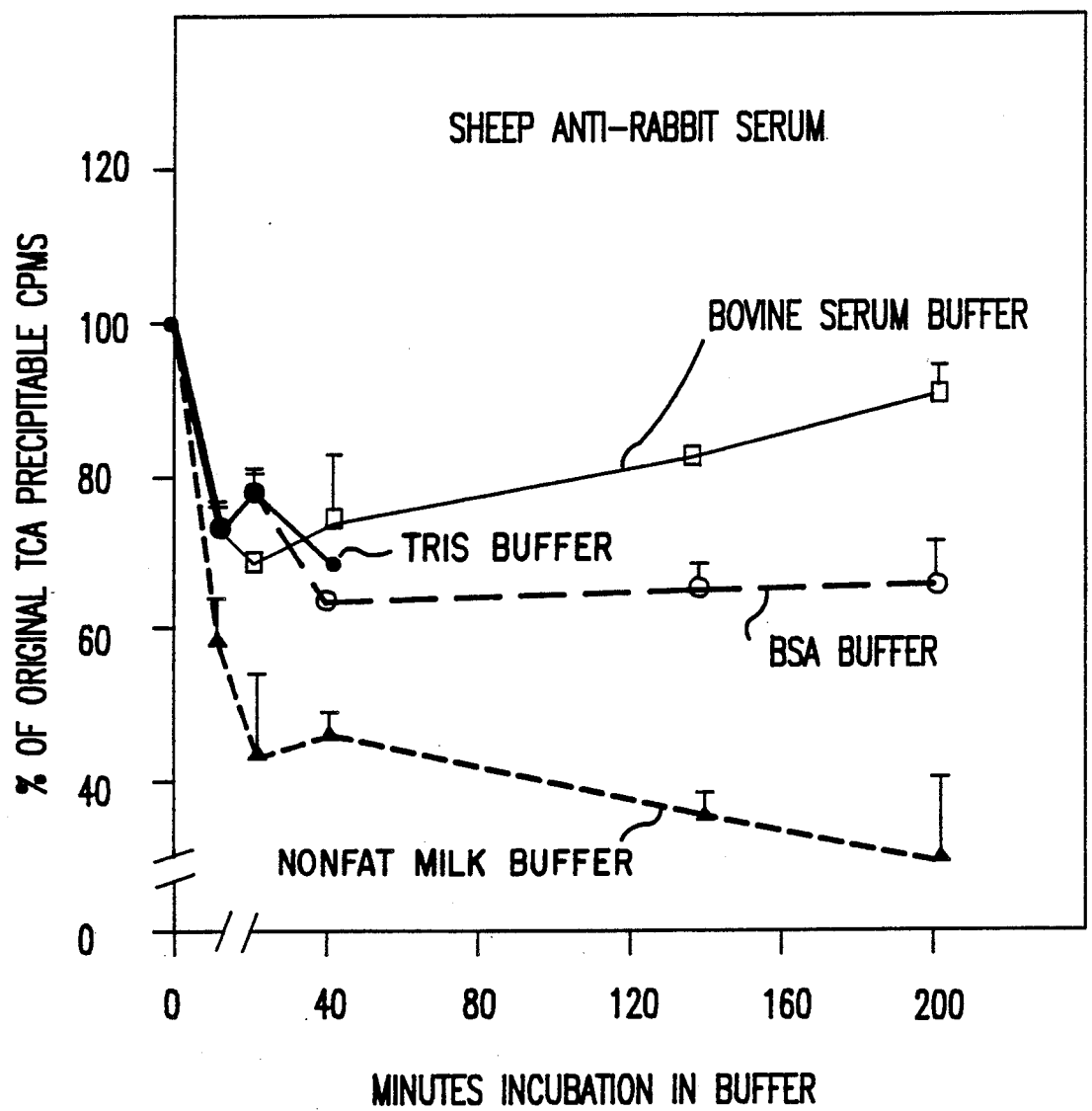

In order to extend the lower range of the standard curve, multiple sample loading was investigated. Iodinated protein samples were spotted onto a sheet of nitrocellulose at intervals of approximately 10 minutes and allowed to dry. The resulting total concentration on the filter was 1:10, 1:9, 1:8, 1:7, and 1:6 relative to undiluted serum. The sheet was then incubated in 10% bovine serum wash buffer for 20 minutes, shaking at room temperature, and washed 3 times for 2 minutes each. The nitrocellulose spots were punched into 7 millimeter disks, and counted for radioactivity. A plot of the amount of bound radioactivity against the number of loadings appears in FIG. 4. The amount of protein that can be multiply loaded deviated from linearity after the 3rd addition. Four or more sample loadings resulted in nonlinearity of the curve due to the saturation of the binding sites.

Up to 10 multiple loadings were attempted over a range of serum concentrations (25 mg/ml to 1 ug/ml), followed by titration of free sites. If the total amount of applied protein was under the capacity of the paper, all standard points were equally displaced by a percentage increase in mean counts over that obtained for a single addition. There was a linear relationship between the number of loadings and the amount of bound radioactivity. Compared to the once loaded values, twice loaded samples were 87.8±6.2%, five times loaded were 84.2±10.3%, and ten times loaded samples were 72.8+6.0%. Thus, multiple loadings are quantitative if (a) the capacity of the nitrocellulose is not exceeded, and (b) the samples are air dried between applications.

The effect of increasing the sample volume was also explored. Nitrocellulose squares (1 cm$^2$) were spotted with 5–20 ul of sample protein. A 20 ul sample actually resulted in an increased signal compared to a 5 ul sample. However, a 80 ul sample yielded poorly reproducible results.

EXAMPLE 4

Stability of the Sample Protein on Nitrocellulose

In order to determine the stability of nitrocellulose-bound proteins during washing and titration steps, the following procedure was performed. Bovine serum buffer (10%) was spiked with serial dilutions of iodinated azocasein (to a 1:128 dilution) and spotted (5 ul) onto a nitrocellulose sheet. After a 20 minute incubation with 10% bovine serum, the samples were washed three times in homologous wash buffer. A mean value for the eight dilution duplicates was 89.6+6% of the counts applied to the nitrocellulose remaining after incubation. This diminution was not significantly different from 100±6% (trichloracetic acid (TCA) precipitated parallel samples). Thus, there was not a significant elution of iodinated azocasein from the nitrocellulose under these conditions.

In another experiment, 5 ul samples of iodinated proteins (sheep anti-rabbit sera, rabbit IgG, azocasein, and molecular weight marker proteins) were incubated with different titration buffers (5% nonfat milk, 3% BSA, 10% bovine serum, or protein-free Tris) for periods up to 200 minutes. The spots were then harvested and counted for radioactivity. The results, expressed as a percentage of the TCA precipitable counts added initially in the 5 ul aliquot, appear in FIG. 5. A very rapid loss of radioactivity was apparent within the first 20 minutes of incubation, which, except for milk buffer, did not diminish further. This data confirms that proteins may be eluted from nitrocellulose by competitive elution by buffer proteins with higher affinities. Thus, matching the affinity of the titrating protein with the analyte is important, especially for longer incubations.

EXAMPLE 5

Comparison of Different Titrating and Wash Buffers

Three titrating buffers containing carrier protein (5% nonfat milk, 3% BSA, 10% bovine serum) were compared for efficacy. The samples (5 ul) were spotted onto a sheet of nitrocellulose. The samples were then incubated for 3 hours in the buffer as indicated in Table 1. Each buffer was spiked with the same amount of iodinated sheep anti-rabbit serum (10870±113 cpm/100 ul). Samples were then washed three times for 2 minutes each in homologous wash buffer before counting radioactivity. Table shows the data expressed as cpms for each sample.

TABLE 1

| Standard | Blocker | | |
|---|---|---|---|
| | Nonfat Milk | Serum | BSA |
| Blank | 375 ± 25 | 1317 ± 300 | 1612 ± 25 |
| Undiluted | 130 ± 15 | 1372 ± 47 | 1192 ± 22 |

The total amount of radioactivity present in the samples titrated with nonfat milk buffer was approximately 1/6th that present in the other titration buffers.

EXAMPLE 6

Time Course of Titration of Free Sites

Figure 6:
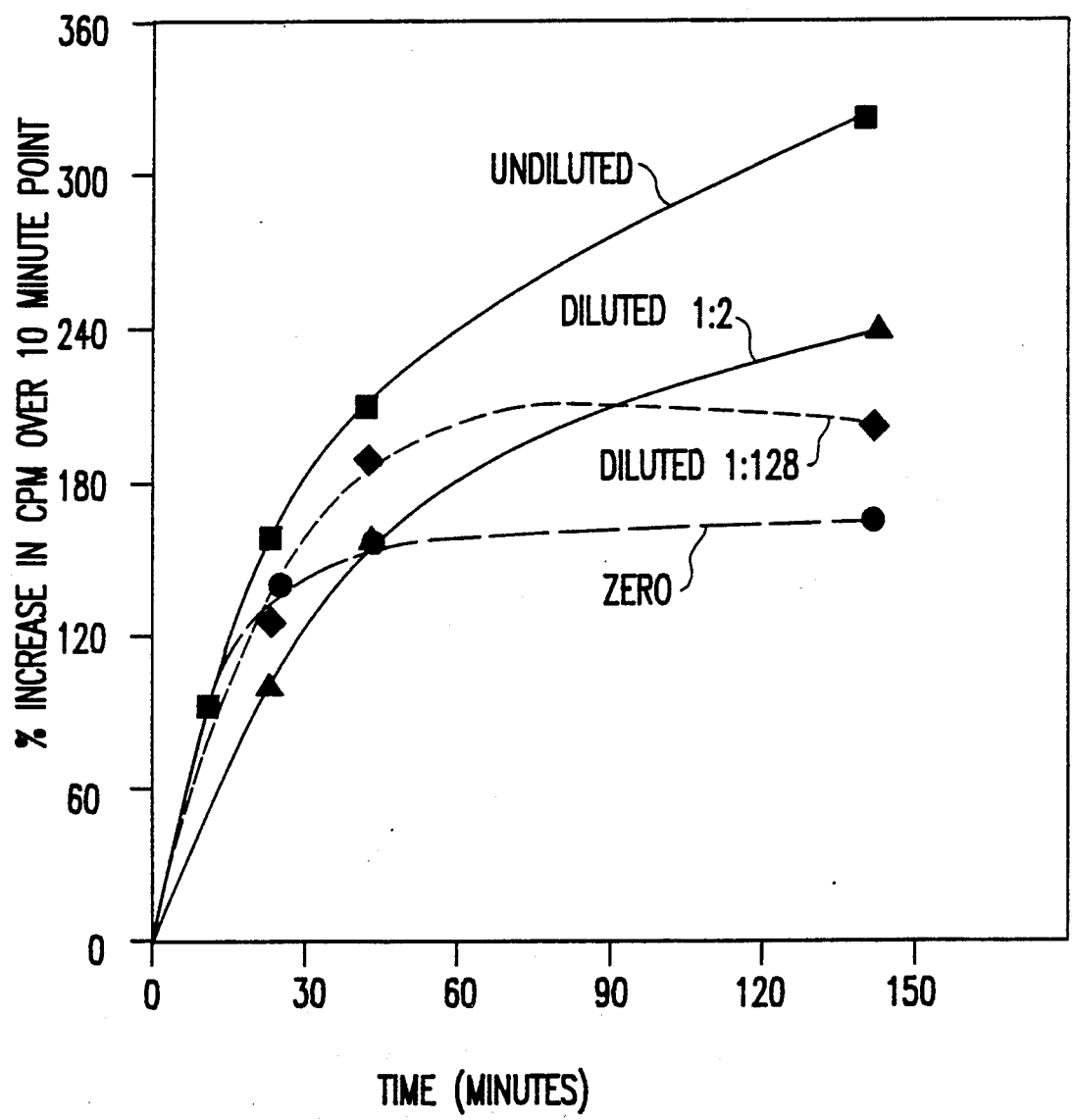
FIG. 6. This figure shows the percentage increase over time of immobilized radioactivity for undiluted, 1:2 diluted, 1:128 diluted, and a blank sample of sheep antirabbit serum protein which was blotted onto nitrocellulose.

Five microliter samples of sheep anti-rabbit serum protein were spotted onto nitrocellulose. Three serum dilutions corresponding to a protein concentration of 70, 35, 0.54 and 0 mg/ml were incubated in bovine serum buffer spiked with iodinated azocasein (36228 cpm/100 ul) for 0, 30, 60, 80, 120 and 150 minutes. Samples were then washed three times for 2 minutes each in homologous wash buffer before being harvested and counted for radioactivity. The results are reported in FIG. 6. The lower the concentration of sample protein spotted onto the nitrocellulose, the more rapid the unoccupied free sites became saturated. Conversely, when the sample protein concentration was high, the maximal absorption of label took longer. The standard deviations of the data presented in FIG. 6 are less than 7%.

Figure 7:
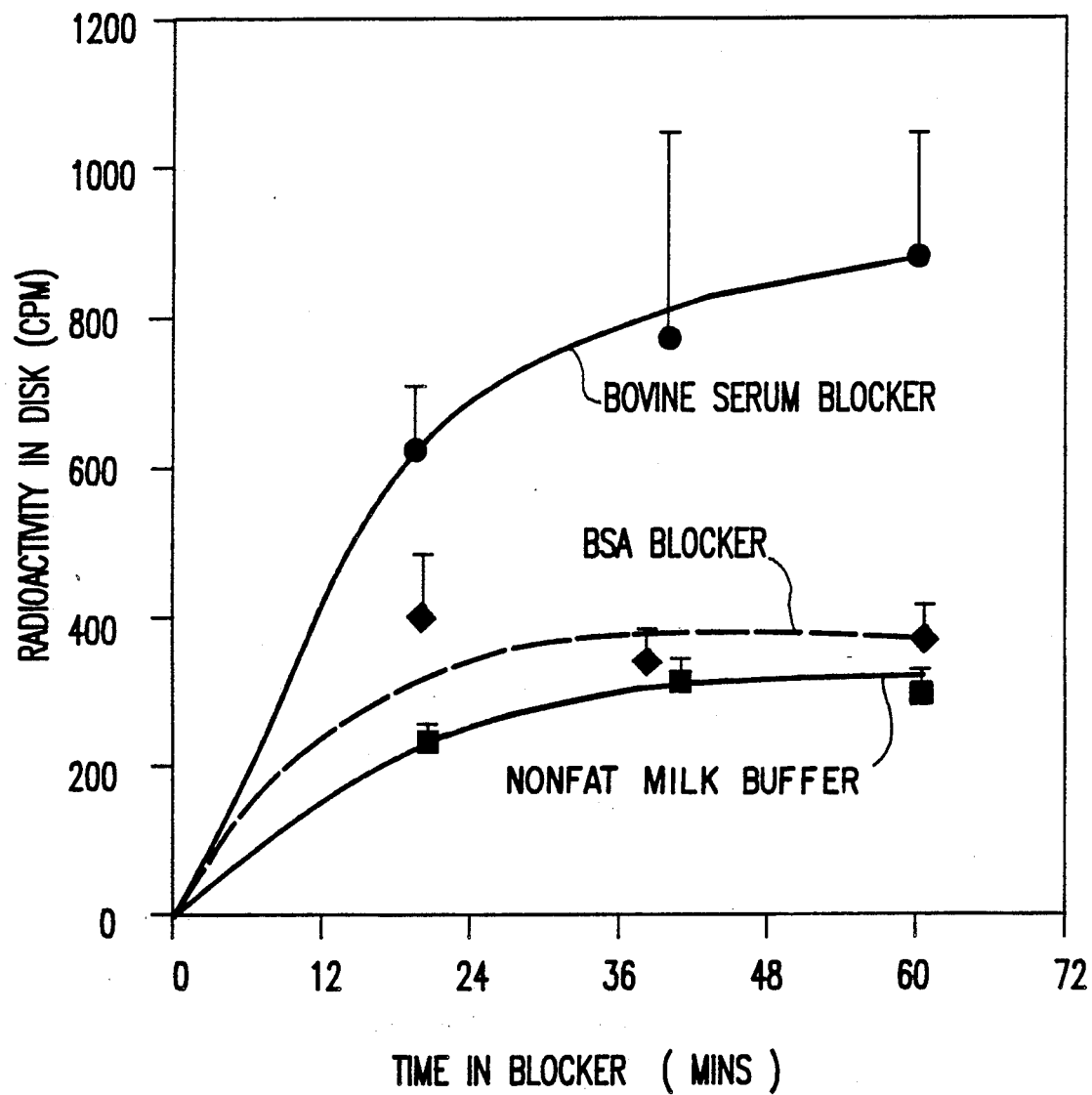
FIG. 7. This figure shows the amount of bound radioactivity on nitrocellulose disks incubated first in nonfat milk blocker, bovine serum blocker or bovine serum albumin blocker followed by incubation with iodinated rabbit IgG.

Different blockers were then compared by incubating disks of nitrocellulose in ml of the protein buffers (nonfat milk blocker, bovine serum blocker, and BSA blocker) in 12×75 mm test tubes for the time specified in FIG. 7. The buffers were then aspirated and 1 ml of Tris buffer vortexed with the disk twice to wash. Tris buffer (1 ml) spiked with iodinated rabbit IgG was then incubated with the disk for 30 minutes. The disks were then washed three times with 1 ml of Tris buffer and the amount of radioactivity remaining on the disks determined. The results are reported in FIG. 7. Nonfat milk and BSA both saturated the maximal number of sites in about 20 minutes, and left a comparable number of free sites. In contrast, bovine serum blocker blocked fewer sites and at a slower rate.

EXAMPLE 7

Isotooe Concentration in Titration Buffer

Figure 8:
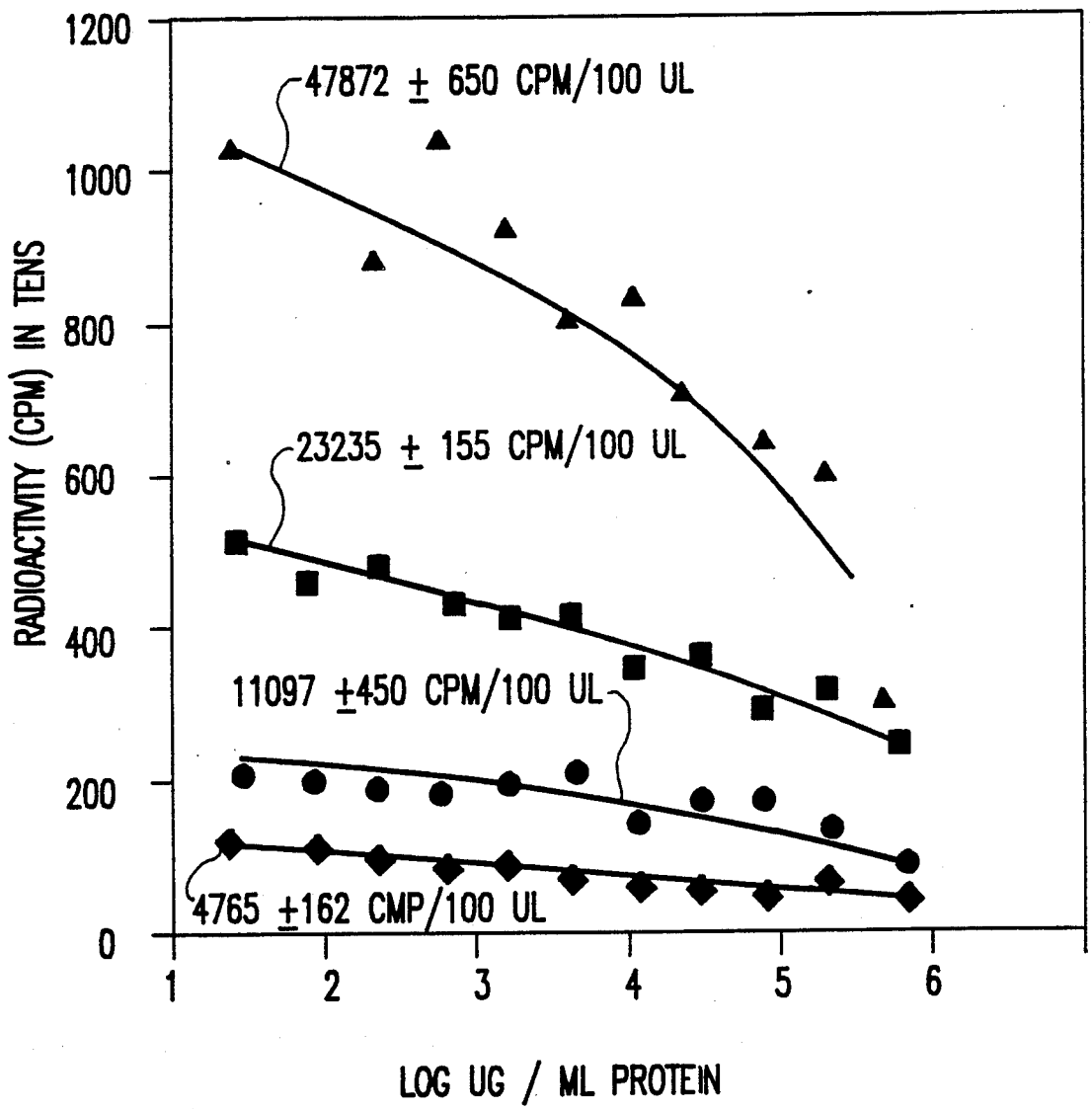
FIG. 8. This figure shows the effect of varying titration buffer tracer concentration while maintaining the same sample protein concentrations.
Figure 9:
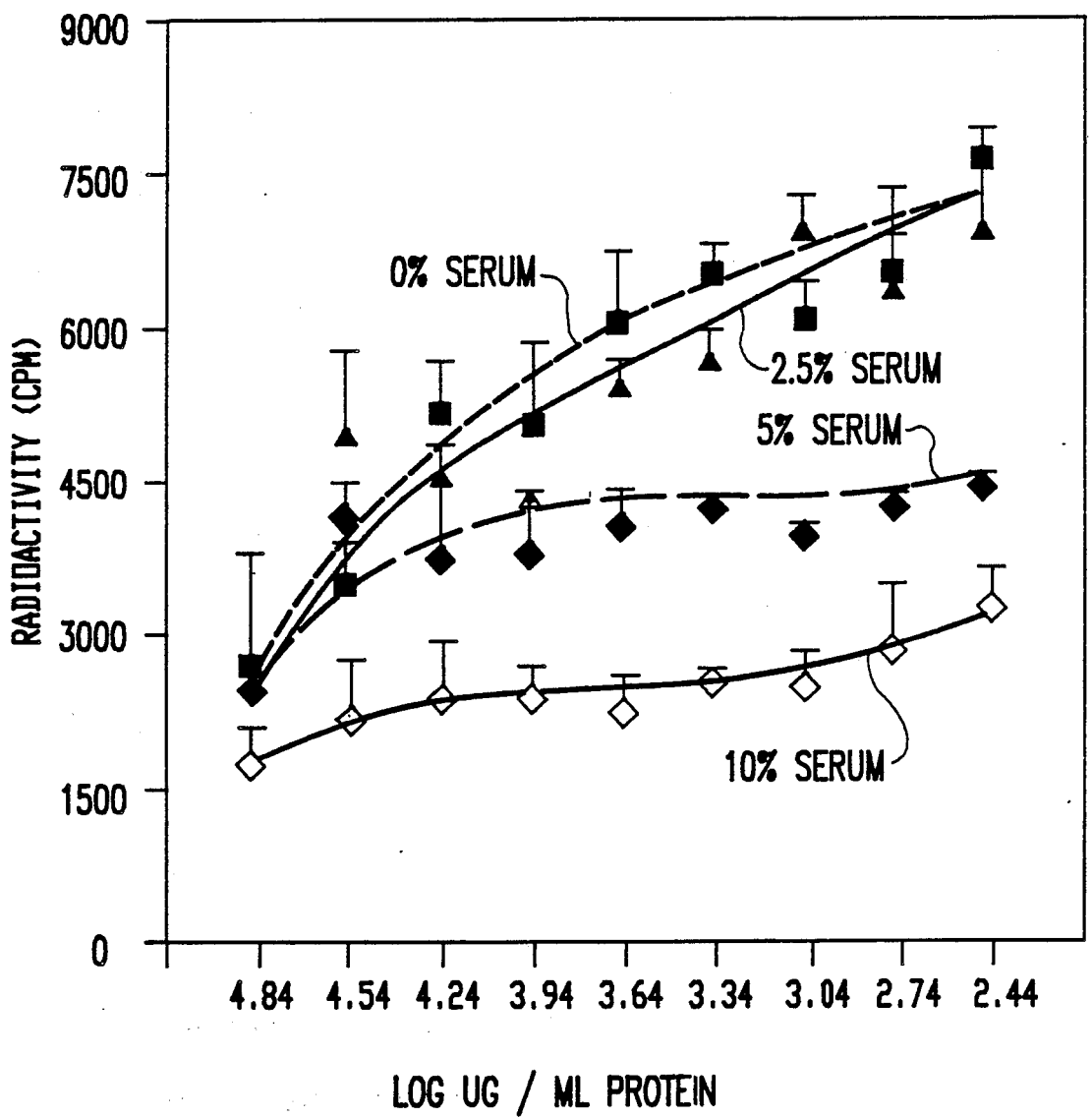
FIG. 9. This figure shows the effect of adding 10%, 5%, 2.5%, or 0% bovine serum buffer containing iodinated azocasein to serial dilutions of sheep anti-rabbit serum spotted onto nitrocellulose.

The effects of varying the titration buffer tracer concentration, while maintaining the same protein concentration, were investigated. 5 ul volumes of sheep anti-rabbit serum protein standards (diluted to give a range of concentrations from 70 mg/ml to 4 ug/ml) were spotted onto nitrocellulose and cut into separate strips for incubation in 10% bovine serum buffer spiked with different amounts (serial dilutions) of iodinated azocasein. The strips were incubated 20 minutes while shaking vigorously. The strips were then washed three times in 10% bovine serum buffer for 2 minutes each, punched out into disks and counted for radioactivity. Results appear in FIG. 8. As the cpm/100 ul of tracer increased, so did the number of counts incorporated into the nitrocellulose binding sites. The relationship between the cpm/100 ul blocker was linear within the range of the curve. The range of the standard curve in cpms between the top (undiluted serum) standard and the zero point was computed to be $y = 0.46x$, where $y$ = the cpm range of the standard curve and $x$ = cpms/100 ul in the blocker.

The effect of keeping the titration buffer cpm/100 ml the same while varying the cold protein concentration using the same system described above was then investigated. Sheep anti-rabbit serum was serially diluted to between 70 mg/ml and 224 ug/ml. Five ul aliquots were spotted onto nitrocellulose, and incubated for 20 minutes in either 10%, 5%, 2.5% or 0% bovine serum buffer spiked with equivalent amounts of iodinated azocasein (18,017+1820 cpm/100 ul). The samples were then washed three times for 2 minutes each in 10% bovine serum wash buffer and the sample/disks harvested for counting. Serum concentrations under 2.5% resulted in curves similar to the 0% serum, which permitted the maximal signal amplitude. As the isotope-carrier ratio increased, the number of counts incorporated into the samples increased, as did the range of the curve. However, this effect was most ked between 5-2.5% serum concentration. Concentrations less than 2.5% or greater than 5% showed relatively smaller changes. This may be due to a minor serum component with a high binding affinity for nitrocellulose which is essentially diluted out at 2.5% serum and is maximally competitive at approximately 5% serum.

EXAMPLE 8

Comparison of Different Protein Standard Curves

Four different proteins (BSA, lysozyme, IgG, and casein) were compared as standards. The titrating buffer was protein free Tris buffer spiked with iodinated molecular weight marker proteins or azocasein. Lysozyme apparently failed to adhere. BSA and casein exhibited strongly adhesive properties under these conditions, while IgG adhered less strongly. These data demonstrate that different proteins have different nitrocellulose binding characteristics.

Having now fully described this invention, it will be appreciated by those skilled in the art that the same can be performed within a wide range of equivalent parameters, concentrations and conditions without departing from the spirit and scope of the invention or any embodiment thereof.

What is claimed is:

1. A method for quantitating a protein analyte in a sample, comprising:
   a) contacting a sample suspected of containing the protein analyte onto an immunologically unreactive solid phase support having binding sites thereon for a sufficient amount of time to effect immogilization of the protein analyte, wherein said protein analyte is bound directly to said solid phase support without the aid of an intermediate binding molecule;
   b) contacting said solid phase support with a detectably labeled titrating protein to bind to all the binding sites on said solid phase support unoccupied by the protein analyte;
   c) incubating said detectably labeled titrating protein with said support for a sufficient amount of time to allow said titrating protein to bind to said binding sites on said solid phase support unoccupied by the protein analyte;
   d) separating said solid support from the incubation mixture obtained in step c); and
   e) detecting the bound titrating protein and thereby detecting and quantifying the protein analyte.

2. The method of claim 1, wherein said solid phase support is selected from the group consisting of nitrocellulose, diazocellose, diazocellulose, dextran, microtiter plates, glass, polyvinylchloride, polystyrene, polypropylene, polyethylene, starch, sepharose, agar, and nylon.

3. The method of claim 1, wherein said solid phase support is diazocellose or nitrocellulose.

4. The method of claim 1, wherein said detectable label is selected from the group consisting of a radioactive isotope, a fluorescent label, a bioluminescent compound, a dye, and an enzyme.

5. The method of claim 1, wherein said protein analyte is recovered by elution with a chaotropic salt after said bound titrating protein is detected in step e.

* * * * *